United States Patent
Hessler

(10) Patent No.: US 7,886,951 B2
(45) Date of Patent: Feb. 15, 2011

(54) POUCH USED TO DELIVER MEDICATION WHEN RUPTURED

(75) Inventor: Thomas R. Hessler, Bethel, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 261 days.

(21) Appl. No.: 12/276,598

(22) Filed: Nov. 24, 2008

(65) Prior Publication Data

US 2010/0127039 A1   May 27, 2010

(51) Int. Cl.
*A61B 17/068* (2006.01)

(52) U.S. Cl. .................. 227/175.1; 227/19; 227/176.1; 606/139; 606/143; 606/151; 606/219

(58) Field of Classification Search ................ 227/19, 227/176.1, 175.1, 180.1; 606/139, 143, 151, 606/219

See application file for complete search history.

(56) References Cited

U.S. PATENT DOCUMENTS

| | | | |
|---|---|---|---|
| 3,079,606 A | 3/1963 | Bobrov et al. | |
| 3,490,675 A | 1/1970 | Green et al. | |
| 3,499,591 A | 3/1970 | Green | |
| 4,429,695 A | 2/1984 | Green | |
| 4,873,977 A | 10/1989 | Avant et al. | |
| 5,065,929 A | 11/1991 | Schulze et al. | |
| 5,156,613 A | 10/1992 | Sawyer | |
| 5,156,614 A | 10/1992 | Green et al. | |
| 5,254,113 A | 10/1993 | Wilk | |
| 5,318,531 A | 6/1994 | Leone | |
| 5,392,979 A | 2/1995 | Green et al. | |
| 5,397,324 A * | 3/1995 | Carroll et al. ............... | 606/139 |
| 5,433,721 A * | 7/1995 | Hooven et al. ............... | 606/143 |
| 5,465,896 A | 11/1995 | Allen et al. | |
| 5,542,594 A | 8/1996 | McKean et al. | |
| 5,554,119 A | 9/1996 | Harrison et al. | |
| 5,611,775 A | 3/1997 | Machold et al. | |
| 5,669,934 A | 9/1997 | Sawyer | |
| 5,690,675 A | 11/1997 | Sawyer et al. | |
| 5,749,895 A | 5/1998 | Sawyer et al. | |
| 5,799,857 A | 9/1998 | Robertson et al. | |
| 5,824,015 A | 10/1998 | Sawyer | |

(Continued)

FOREIGN PATENT DOCUMENTS

EP   0 577 373 A2   1/1994

(Continued)

OTHER PUBLICATIONS

European Search Report for EP 09252665.6-1269 date of completion is Jan. 20, 2010 (3 pages).

*Primary Examiner*—Scott A. Smith

(57) ABSTRACT

An anvil assembly for a circular stapling device includes an anvil head configured to support an anvil plate thereon, a shaft extending from the anvil head and configured to selectively engage a rod member of the circular stapling device, an anvil plate operatively connected to the anvil head, wherein the anvil plate includes an inner diametral edge, and wherein the anvil plate defines a plurality of staple forming pockets therein at a location radially outward of the inner diametral edge, a recess formed in the anvil head, wherein the recess is defined by the inner diametral edge of the anvil plate and a rear surface of the anvil head, and a wound treatment material disposed substantially within the recess.

20 Claims, 17 Drawing Sheets

U.S. PATENT DOCUMENTS

| | | | |
|---|---|---|---|
| 5,843,033 A | 12/1998 | Ropiak | |
| 5,866,561 A | 2/1999 | Ungs | |
| 5,895,412 A | 4/1999 | Tucker | |
| 5,915,616 A | 6/1999 | Viola et al. | |
| 5,931,165 A | 8/1999 | Reich et al. | |
| 5,964,394 A | 10/1999 | Robertson | |
| 6,032,849 A | 3/2000 | Mastri et al. | |
| 6,045,560 A | 4/2000 | McKean et al. | |
| 6,149,641 A | 11/2000 | Ungs | |
| 6,165,201 A | 12/2000 | Sawhney | |
| 6,179,862 B1 | 1/2001 | Sawhney | |
| 6,228,051 B1 | 5/2001 | Trumbull | |
| 6,287,323 B1 | 9/2001 | Hammerslag | |
| 6,398,797 B2 | 6/2002 | Bombard et al. | |
| 6,451,029 B1 | 9/2002 | Yeatman | |
| 6,488,197 B1 | 12/2002 | Whitman | |
| 6,491,201 B1 | 12/2002 | Whitman | |
| 6,589,269 B2 | 7/2003 | Zhu et al. | |
| 6,592,597 B2 | 7/2003 | Grant et al. | |
| 6,623,452 B2 | 9/2003 | Chien et al. | |
| 6,656,193 B2* | 12/2003 | Grant et al. | 606/151 |
| 6,681,979 B2 | 1/2004 | Whitman | |
| 6,695,199 B2 | 2/2004 | Whitman | |
| 6,704,210 B1* | 3/2004 | Myers | 361/773 |
| 6,835,336 B2 | 12/2004 | Watt | |
| 6,838,493 B2 | 1/2005 | Williams et al. | |
| 6,846,308 B2 | 1/2005 | Whitman et al. | |
| 6,867,247 B2 | 3/2005 | Williams et al. | |
| 7,032,798 B2 | 4/2006 | Whitman et al. | |
| 7,066,934 B2 | 6/2006 | Kirsch | |
| 7,070,083 B2* | 7/2006 | Jankowski | 227/176.1 |
| 7,141,055 B2 | 11/2006 | Abrams et al. | |
| 7,217,254 B2 | 5/2007 | Kirwan et al. | |
| 7,238,195 B2* | 7/2007 | Viola | 606/219 |
| 7,296,722 B2* | 11/2007 | Ivanko | 227/175.1 |
| 7,334,717 B2* | 2/2008 | Rethy et al. | 227/175.1 |
| 2003/0111507 A1 | 6/2003 | Nunez | |
| 2003/0236518 A1 | 12/2003 | Marchitto et al. | |
| 2005/0038471 A1 | 2/2005 | Chan et al. | |
| 2005/0043678 A1 | 2/2005 | Freyman et al. | |
| 2006/0085033 A1 | 4/2006 | Criscuolo | |
| 2006/0108393 A1 | 5/2006 | Heinrich et al. | |

FOREIGN PATENT DOCUMENTS

| | | |
|---|---|---|
| EP | 1647230 A1 | 4/2006 |
| WO | 90/05489 A1 | 5/1990 |
| WO | 00/56376 | 9/2000 |
| WO | 01/62158 A2 | 8/2001 |
| WO | 01/62162 A1 | 8/2001 |
| WO | 02/30297 | 4/2002 |
| WO | 03/088844 A1 | 10/2003 |
| WO | 03/094743 A1 | 11/2003 |
| WO | 03/094746 A1 | 11/2003 |
| WO | 03/105698 A2 | 12/2003 |
| WO | WO2006/044490 A2 | 4/2006 |

\* cited by examiner

POUCH USED TO DELIVER MEDICATION WHEN RUPTURED

BACKGROUND

1. Technical Field

The present disclosure relates to surgical devices for enhancing properties of tissue repaired or joined by surgical staples and, more particularly, to surgical devices suitable for performing circular anastomosis of hollow organs and methods for enhancing properties of tissue repaired or joined by surgical staples.

2. Discussion of Related Art

Anastomosis is the surgical joining of separate hollow organ sections. The site of the attachment is also sometimes called an anastomosis. Typically, an anastomosis procedure follows surgery in which a diseased or defective section of a hollow organ is removed and the remaining end sections are to be joined. Depending on the desired anastomosis procedure, the end sections may be joined by either circular, end-to-end, end-to-side or side-to-side organ reconstruction methods.

End-to-end anastomosis is generally performed using surgical staples. The staples are usually left in the patient. In a circular anastomosis procedure, the two ends of the organ sections may be joined by means of a stapling instrument which drives a circular array of staples through the organ end sections and simultaneously cores and removes any tissue located interior of the driven circular array of staples to free a tubular passage.

In some applications of a circular anastomosis procedure, an anvil rod having an attached anvil head is mounted to the distal end of a surgical stapling instrument shaft prior to insertion of the instrument into the tissue to be anastomosed. However, in other applications, it is preferable to utilize a detachable anvil rod which may be mounted to the instrument subsequent to positioning of the instrument and the anvil assembly within respective tissue sections. In such instances, the stapling instrument and the anvil assembly are separately delivered to the operative site. Each tissue section is secured to a respective anvil or staple holding component by a purse string suture. The anvil assembly is mounted to the stapling instrument by inserting a mounting portion of the anvil rod within the distal end of the instrument so that a mounting mechanism within the instrument securely engages the rod.

Certain surgical procedures utilize pledgets, buttresses or other types of biocompatible surgical fabrics and reinforcement materials. Buttresses are typically placed over the tissue-contacting surface of the anvil and/or the tissue-contacting surface of the staple holding component and secured against the target tissue during the firing of the surgical stapling instrument.

Other surgical procedures involve the step of applying (e.g., by spraying, brushing, etc.) an adhesive material and/or a sealant material to the external surface of the target surgical site following the surgical stapling procedure.

Still other procedures include the use of biological tissue adhesives. Biological adhesives generally bond separated tissues together to aid in the healing process and to enhance the tissue strength and may be used instead of suturing and stapling, for example, in surgical procedures for the repair of tissue or the creation of anastomoses. Generally, the use of biocompatible adhesives tends to minimize foreign body reaction and scarring.

SUMMARY

The present disclosure relates to an anvil assembly for a circular stapling device. The anvil assembly includes an anvil head configured to support an anvil plate thereon, a shaft extending from the anvil head and configured to selectively engage a rod member of the circular stapling device, and an anvil plate operatively connected to the anvil head, wherein the anvil plate includes an inner diametral edge, and wherein the anvil plate defines a plurality of staple forming pockets therein at a location radially outward of the inner diametral edge. The anvil assembly also includes a recess formed in the anvil head and a wound treatment material disposed substantially within the recess, wherein the recess is defined by the inner diametral edge of the anvil plate and a rear surface of the anvil head.

The recess formed in the anvil head may have a diameter larger than a diameter of a knife blade that is longitudinally moveable along the shaft, wherein the wound treatment material delivery pouch is at least partially axially aligned with the knife blade.

The wound treatment material may be contained in at least one wound treatment material delivery pouch. The wound treatment material may be disposed within an annular pouch.

The wound treatment material may be an adhesive, a sealant, a hemostat and/or a medicament. The adhesive may include an adhesive which cures upon tissue contact, an adhesive which cures upon exposure to ultraviolet (UV) light, and/or an adhesive which is pressure sensitive. The adhesive may include a protein derived, aldehyde-based adhesive material and/or a cyanoacrylate-based material. The sealant material may include a fibrin sealant material, a collagen-based and synthetic polymer-based tissue sealant material, and/or synthetic polyethylene glycol-based, hydrogel sealant material. The hemostat material may include a fibrin-based material, a collagen-based material, an oxidized regenerated cellulose-based material, a gelatin-based material and/or a fibrinogen-thrombin material. The medicament may include drugs, enzymes, growth factors, peptides, proteins, dyes and/or diagnostic agents.

The anvil assembly may also include a wound treatment material disposed in each staple forming pocket of the anvil plate. The anvil assembly may also include a liner covering the plurality of staple forming pockets.

According to another exemplary embodiment of the present disclosure, a surgical stapling device includes a handle portion, a body portion located at the distal end of the handle portion, and a head portion located at the distal end of the body portion. The head portion includes an anvil assembly, a staple cartridge assembly and a knife blade. The staple cartridge assembly includes an annular array of staples. The anvil assembly includes an anvil head configured to support an anvil plate thereon, a shaft extending from the anvil head and configured to selectively engage a rod member of the staple cartridge assembly, an anvil plate operatively connected to the anvil head, wherein the anvil plate includes an inner diametral edge having a diameter larger than a diameter of the knife blade, and wherein the anvil plate defines a plurality of staple forming pockets therein, a recess formed in the anvil head, wherein the recess is defined by the inner diametral edge of the anvil plate and a rear surface of the anvil head, and a wound treatment material disposed substantially within the recess.

The wound treatment material may be contained in at least one wound treatment material delivery pouch. The wound treatment material may be contained in a pair of stacked wound treatment material delivery pouches. The pair of stacked wound treatment material delivery pouches may be at least partially axially aligned with the knife blade. At least one of the pair of stacked wound treatment material delivery pouches may include a plurality of compartments.

The wound treatment material may be contained in a plurality of wound treatment material delivery pouches, wherein at least one wound treatment material delivery pouch includes a plurality of compartments.

The surgical stapling device may also include a liner covering the entirety of the recess and disposed over the wound treatment material. At least a portion of the wound treatment material may be contained in a wound treatment material delivery pouch.

BRIEF DESCRIPTION OF THE DRAWINGS

The foregoing features of the present disclosure will become more readily apparent and may be understood by referring to the following detailed description of an illustrated embodiment of a surgical device, taken in conjunction with the accompanying drawings, in which.

DESCRIPTION OF EMBODIMENTS

Figure 1:
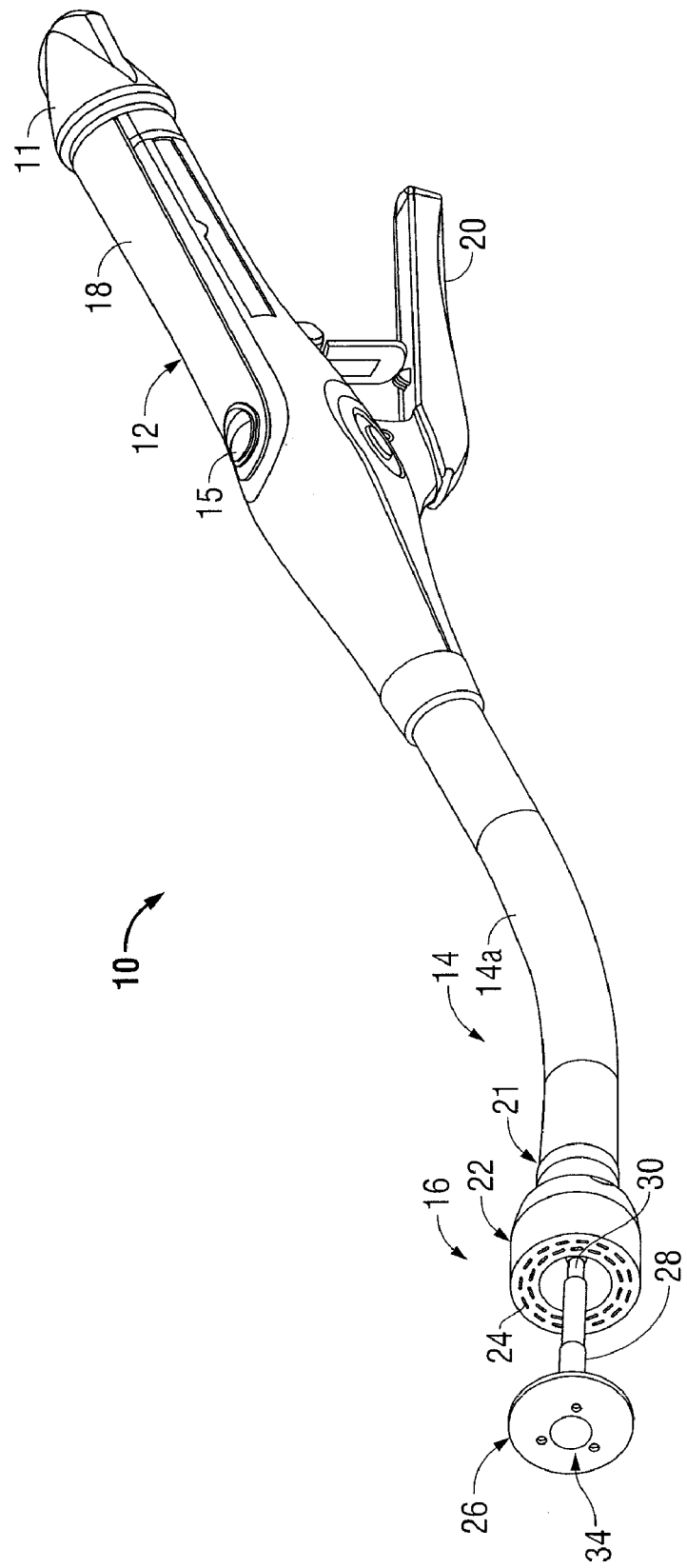
FIG. 1 is a perspective view of a surgical stapling device shown in the unapproximated position, according to an embodiment of the present disclosure.

Hereinafter, exemplary embodiments of the presently disclosed surgical stapling device will be described with reference to the accompanying drawings. Like reference numerals may refer to similar or identical elements throughout the description of the figures. As used herein, the term "proximal" refers to the portion of the instrument closest to the operator and the term "distal" refers to the portion of the instrument furthest from the operator.

FIG. 1 illustrates an embodiment of the presently disclosed surgical stapling device shown generally as 10. Briefly, surgical stapling device 10 includes a proximal handle assembly 12, an elongated central body portion 14 including a curved elongated outer tube 14a, and a distal head portion 16.

Body portion 14 may be constructed so as to have a curved shape along at least a portion of its length, e.g., as shown in FIG. 1. Alternately, in some surgical procedures, e.g., the treatment of hemorrhoids, it is desirable to have a substantially straight, preferably shortened, central body portion. Body portion 14 may be adapted to be flexible to allow the body portion 14 to bend to any configuration. It is to be understood that the body portion 14 and the head portion 16 may be configured in a variety of shapes and sizes depending on a particular surgical purpose or to accommodate a particular surgical need.

Handle assembly 12 includes a stationary handle 18, a firing trigger 20, a rotatable approximation knob 11 and an indicator 15. Stationary handle 18 may be formed from thermoplastics, e.g., polycarbonate, and defines a housing for the internal components of the handle assembly 12. Cushioned and/or resilient slip resistant portions such as a grip (not shown) can be fastened to or included as part of the stationary handle 18 and the firing trigger 20. The slip resistant grip may be formed over the stationary handle 18 and the firing trigger 20, e.g., using an overmolding procedure and may be formed from neoprene or rubber. It is to be understood that other suitable materials, e.g., elastomeric materials, and joining techniques may be employed. Indicator 15 is positioned on the stationary handle 18 and includes indicia, e.g., color coding, alpha-numeric labeling, etc., to identify to a surgeon whether the device is approximated and is ready to be fired. Indicator 15 may have a bulbous or convex shape which extends outwardly from a top surface of the stationary handle 18 and is easily viewable from the top and sides of the stapling device.

Head portion 16 includes an anvil assembly shown generally as 26 in FIGS. 1-18 and a staple cartridge assembly 22. Each of these assemblies will be described herein below. Staple cartridge assembly 22 includes an annular array of staples "S" (see FIGS. 15A-18). Positioned opposite the staple cartridge assembly 22 is an anvil assembly 26 which is connected to the stapling device 10 by the shaft 28. Examples of anvil assembly and staple cartridge assembly embodiments are disclosed in commonly assigned U.S. Pat. No. 5,119,983, issued Jun. 9, 1992, which is incorporated herein by reference in its entirety. Head portion 16 further includes a knife assembly that includes a knife blade 50 (see FIGS. 15A-18), which moves longitudinally along shaft 28 upon firing of the surgical stapling device 10. Examples of knife assembly embodiments are disclosed in commonly assigned U.S. patent application Ser. No. 12/184,298, filed Aug. 1, 2008, which is incorporated herein by reference in its entirety.

The components of the surgical device 10 are generally formed from thermoplastics including polycarbonates, and metals including stainless steel and aluminum. The particular material selected to form a particular component may depend upon the strength requirements of the particular component. For example, the anvil may be formed from a metal, such as stainless steel, and the stationary handle 18 may be formed from a thermoplastic such as polycarbonate. Alternately, other suitable materials not listed above, which preferably can withstand sterilization procedures, may be used to form components of the stapling device 10, e.g., provided the materials are suitable for surgical use and meet the strength requirements of the particular component.

Referring to FIGS. 1-6, the anvil assembly 26 includes an anvil head 34 and a shaft 28 extending from anvil head 34. Anvil head 34 is configured to support an anvil plate 3 thereon. Anvil plate 36 includes a plurality of staple forming pockets 38 formed therein, as shown in FIGS. 2A-5. Staple forming pockets 38 may be arranged in a pair of spaced apart, staggered, concentric annular rings formed in the anvil plate 36. It is to be understood that the shape, size and pattern of the staple forming pockets 38 may be varied from the exemplary configurations depicted in FIGS. 2A, 2B, 3A, 3B, 4 and 5.

Although the stapling device 10 is shown and described as utilizing a staple cartridge assembly 22 having an annular array of staples positioned on the tubular body portion 14, and having the anvil assembly 26 positioned opposite the staple cartridge assembly 22 for movement towards and away from the staple cartridge assembly 22, it is contemplated herein that the anvil assembly 26 may be positioned on the tubular body portion 14 and the staple cartridge assembly 22 and array of staples be positioned opposite the anvil assembly 26 for movement towards and away from the anvil assembly 26.

Figure 14:
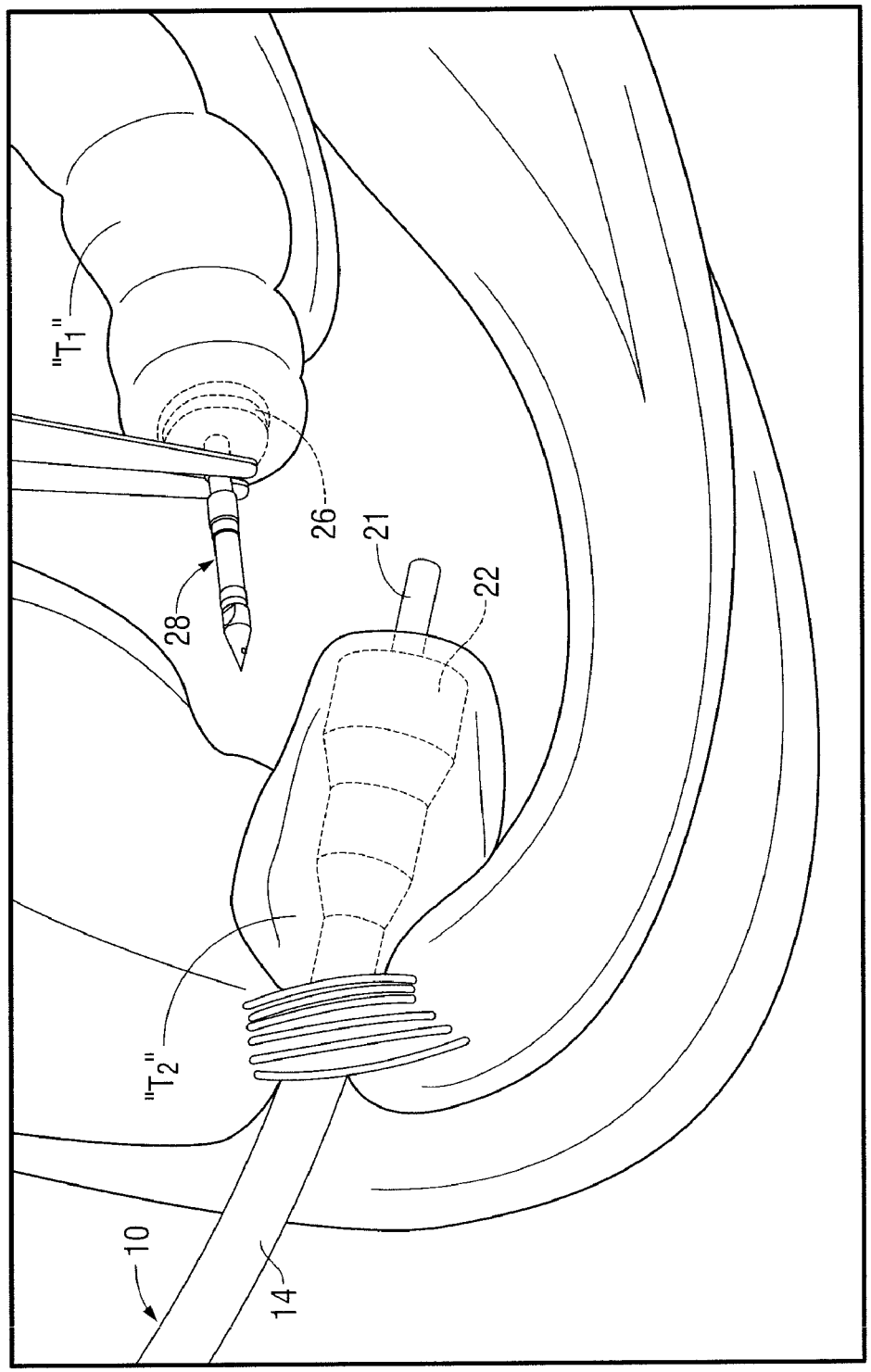
FIG. 14 is a perspective view of the intestinal area of a patient, illustrating a method of positioning an anvil assembly when performing an intestinal anastomosis.

Turning momentarily to FIG. 14, to perform an anastomosis procedure, the stapling device 10 is positioned within a tubular body organ of the patient and the end portions of the organ sections to be joined are positioned in the gap between the staple cartridge assembly 22 and the anvil assembly 26. The two end portions to be joined are secured over the anvil assembly 26 and the staple cartridge assembly 22, respectively, by a purse string suture prior to approximation of the anvil assembly 26 in relation to the staple cartridge assembly 22. With the anvil assembly 26 and the staple cartridge assembly 22 purse string sutured, the shaft 28 of the anvil assembly 26 is coupled to a rod member 21, which extends outward from the distal end of the staple cartridge assembly 22. The proximal end portion of the shaft 28 may include a generally conical shaped mounting portion 30 (shown in FIG. 1) that is advantageously dimensioned to facilitate entry within the rod member 21 and which further enables manipulation of shaft 28 through body tissue. It is to be understood that the proximal end portion of the shaft 28 may include a number of portions having various shapes and dimensions.

In various embodiments of the presently disclosed surgical stapling device 10, in order to approximate the anvil assembly 26 towards the staple cartridge assembly 22, the approximation knob 11 is rotated to displace the rod member 21 in a proximal direction. Displacement of the rod member 21 in the proximal direction draws the anvil assembly 26 into a position adjacent to the staple cartridge assembly 22 and locates the ends of the tissue sections "$T_1$" and "$T_2$" (see FIGS. 14-18) between the anvil assembly 26 and the staple cartridge assembly 22.

Figure 2A:
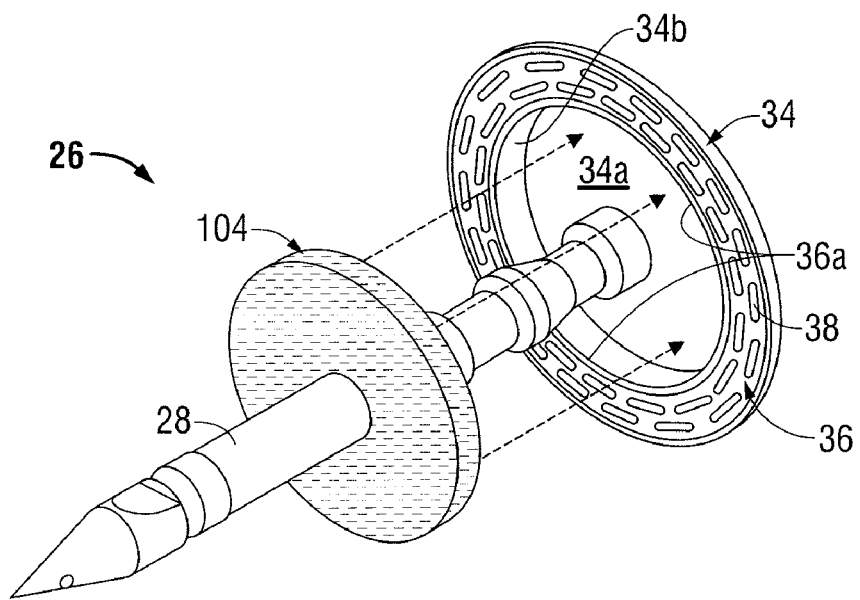
FIG. 2A is a perspective view of the anvil assembly of FIG. 1 showing a wound treatment material delivery pouch, slideably attached to the shaft of the anvil assembly, according to an embodiment of the present disclosure.
Figure 2B:
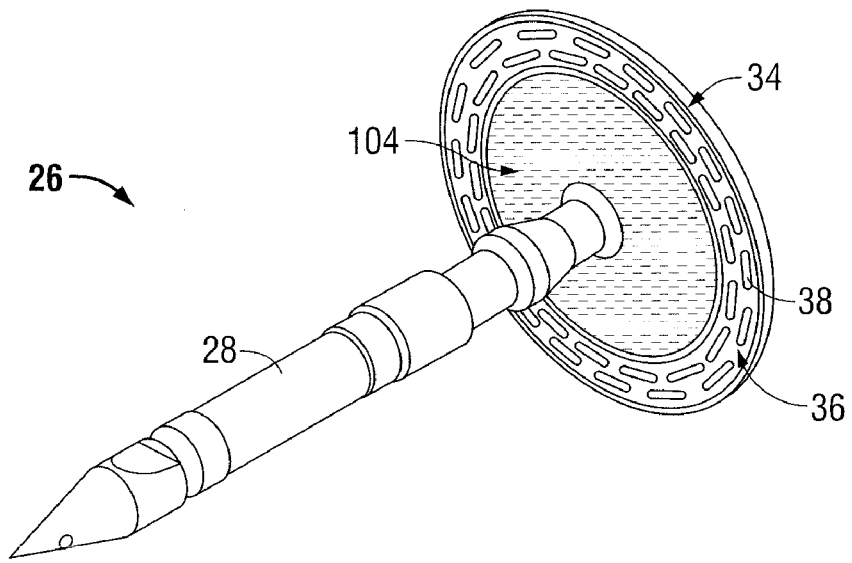
FIG. 2B is a perspective view of the anvil assembly of FIG. 1 showing the wound treatment material delivery pouch illustrated in FIG. 2A located adjacent to the anvil head, in an operative position, according to an embodiment of the present disclosure.

Turning back to FIGS. 1-6, the anvil assembly 26 includes a recess 34b defined by the inner diametral edge 36a of the anvil plate 36 and a rear surface 34a of the anvil head 34. Referring to FIGS. 2A, 2B and 6 the anvil assembly 26 includes a wound treatment material delivery pouch 104, used to deliver or dispense wound treatment material when ruptured, which is located radially inward of the staple forming pockets 38 and at least partially axially aligned with knife blade 50. As shown in FIGS. 2A and 2B, in an embodiment, wound treatment material delivery pouch 104 is located in the recess defined by the inner diametral edge 36a of the anvil plate 36 and the rear surface 34a of the anvil head 34. In operation, when the surgical stapling device 10 is fired, a knife blade 50 (shown in FIGS. 15A-15C) ruptures the wound treatment material delivery pouch 104, whereby the wound treatment material contained within the wound treatment material delivery pouch 104 is dispensed onto or otherwise spread onto the area of the anastomosis site.

Wound treatment material delivery pouch 104 is fabricated from a material that can be penetrated or ruptured by the knife blade 50. For example, the wound treatment material delivery pouch 104 may be fabricated from a polymeric material, such as polyethylene, polyester, polyurethane, or combination thereof, or other suitable material. It is contemplated herein that the wound treatment material delivery pouch 104 is fabricated from a bio-absorbable material so that any portion of the wound treatment material delivery pouch 104 that remains in the patient's body following the surgical procedure will be absorbed into the body. It is to be understood that the shape and size of the pouch 104 may be varied from the exemplary configuration depicted in FIGS. 2A and 2B.

Figure 4:
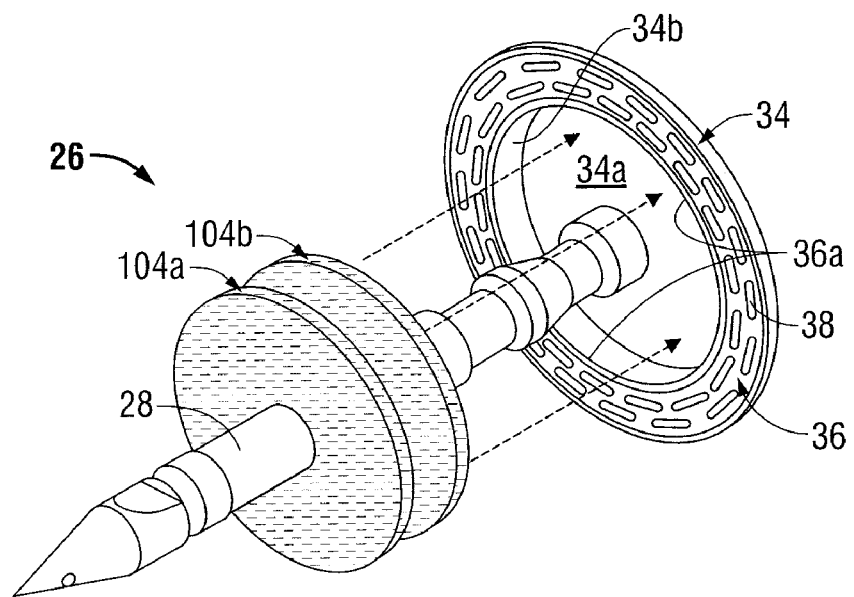
FIG. 4 is a perspective view of the anvil assembly of FIG. 1 including wound treatment material delivery pouches, similar to FIG. 2A, in a stacked configuration, according to an embodiment of the present disclosure.

Wound treatment material within the wound treatment material delivery pouch 104 may include various components, such as, for example, an adhesive, sealant, hemostat and/or other medicament. For example, a sealant component of the wound treatment material within the wound treatment material delivery pouch 104 may function to retard any bleeding which may occur from the tissue, and an adhesive component of the wound treatment material may function to secure the approximated tissue together. As seen in FIG. 4, any number of wound treatment material delivery pouches (two pouches 104a, 104b being shown) may be stacked atop one another to provide a number of layers or pockets of wound treatment material. The number of layers or pockets and the wound treatment material therein may vary depending on a particular surgical purpose, clinical data, patient's medical/surgical history, etc.

It is contemplated herein that the adhesive component may include adhesives that cure upon tissue contact, adhesives that cure upon exposure to ultraviolet (UV) light, pressure sensitive adhesives, or any combination thereof, or any other suitable adhesive. In one embodiment, it is contemplated that an adhesive having a cure time of from about 10 to 15 seconds may be used. In another embodiment, it is contemplated that an adhesive having a cure time of about 30 seconds may be used. It will be appreciated that an adhesive component having any suitable cure time may be employed.

It is contemplated herein that the wound treatment material within the wound treatment material delivery pouch 104 may be a pre-cured adhesive or sealant. A pre-cured sealant or adhesive may react with the moisture and/or heat of the body tissue to thereby activate the sealing and/or adhesive properties of the sealant or adhesive. For example, the pre-cured sealant or adhesive may be a hydro-gel or the like.

Examples of adhesives that can be employed include protein derived, aldehyde-based adhesive materials, e.g., albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of sealants include synthetic polyethylene glycol-based, hydrogel materials sold under the trade designation CoSeal™ by Cohesion Technologies and Baxter International, Inc. Examples of hemostat materials which can be employed include fibrin-based, collagen-based, oxidized regenerated cellulose-based and gelatin-based topical hemostats. Examples of hemostat materials include fibrinogen-thrombin combination materials sold under the trade designations CoStasis™ by Tyco Healthcare Group, LP, and Tisseel™ sold by Baxter International, Inc. Other hemostat materials include astringents, e.g., aluminum sulfate, and coagulants.

Wound treatment material within the wound treatment material delivery pouch 104 may also include medicaments. Such medicaments may include one or more medically and/or surgically useful substances such as drugs, enzymes, growth factors, peptides, proteins, dyes, diagnostic agents or hemostasis agents, e.g., any pharmaceutical used in the prevention of stenosis.

Figure 3A:
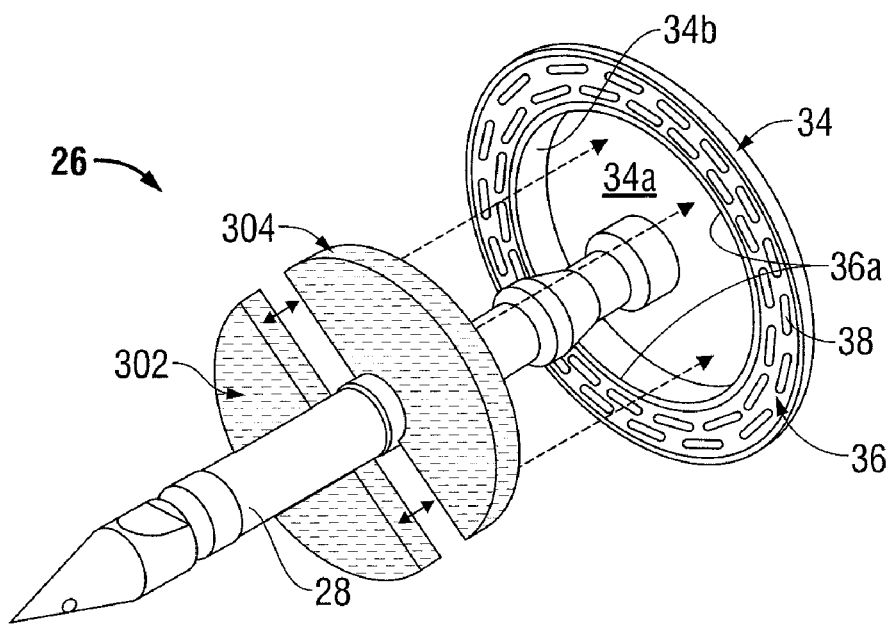
FIGS. 3A and 3B are perspective views of the anvil assembly of FIG. 1 and a wound treatment material delivery pouch, according to another embodiment of the present disclosure.
Figure 3B:
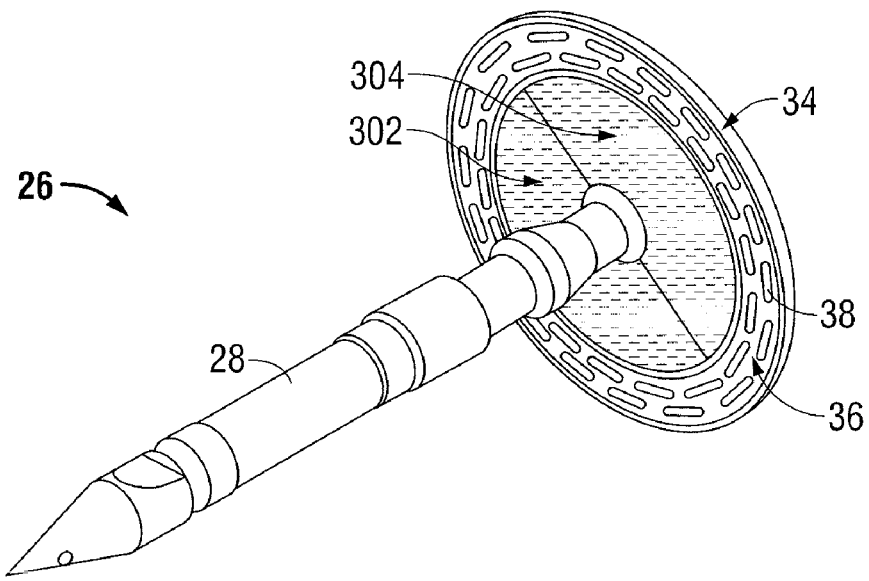

In another embodiment of the present disclosure illustrated in FIGS. 3A and 3B, anvil assembly 26 includes two substantially C-shaped wound treatment material delivery pouches 302 and 304. Each wound treatment material delivery pouch 302, 304 is fabricated from a material that can be penetrated or ruptured by the knife blade 50. The wound treatment material within the wound treatment material delivery pouch 302 may be different than the wound treatment material within the wound treatment material delivery pouch 304. Either one (or both) of the wound treatment material delivery pouches 302, 304 may be adapted to include a number of layers or pockets of wound treatment material, e.g., depending on a particular surgical purpose, clinical data, patient history's medical/surgical, etc. Although the wound treatment material delivery pouches 302, 304 are shown as separate components in FIG. 3A, it is to be understood that the wound treatment material delivery pouches 302, 304 may be joined, e.g., bonded or fused together, to form a single component having two pockets or compartments for containing wound treatment material. The wound treatment material contained the wound treatment material delivery pouches 302, 304 may include two-part components, e.g., epoxy and resin, which become active upon mixing thereof. It is further contemplated that while two pouches 302, 304 are shown, that any number of pouches may be provided.

Figure 5:
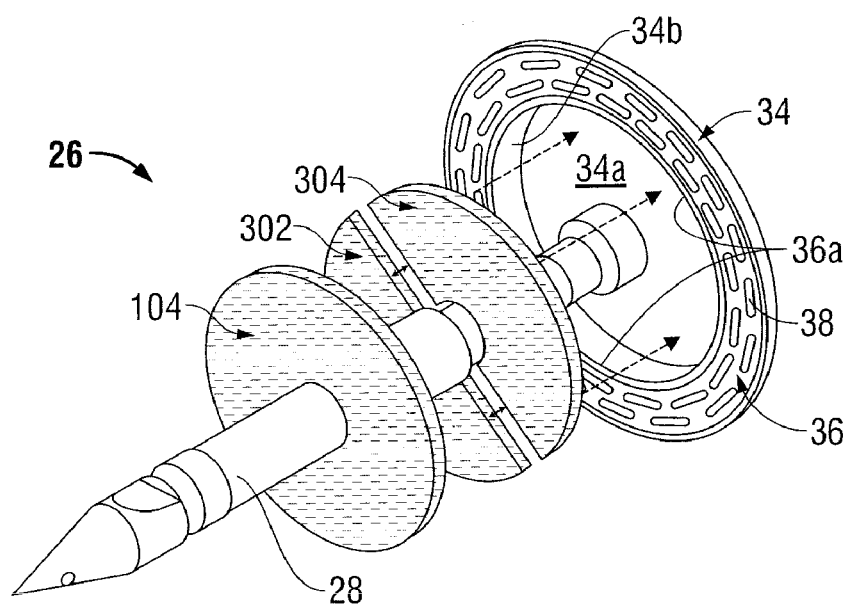
FIG. 5 is a perspective view of the anvil assembly of FIG. 1 including wound treatment material delivery pouches, similar to FIGS. 2A and 3A, in a stacked configuration, according to the present disclosure.
Figure 6:
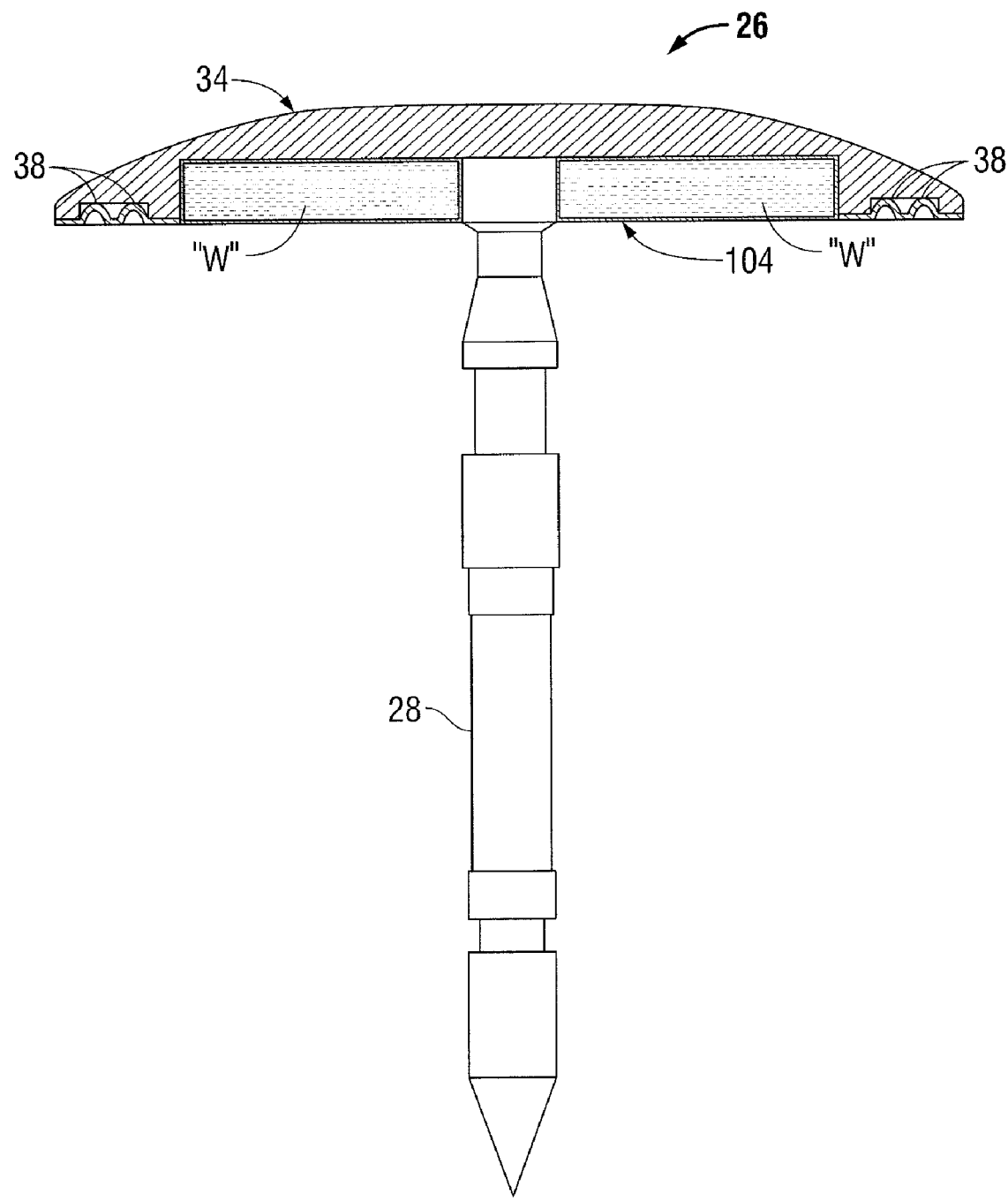
FIG. 6 is a cross-sectional view of the anvil assembly of FIGS. 2A and 2B.

FIGS. 4 and 5 show the anvil assembly of FIG. 1 including multiple layers of wound treatment material delivery pouches, in a stacked configuration, according to embodiments of the present disclosure. As shown in FIG. 4, and as mentioned above, in an embodiment, two wound treatment material delivery pouches 104a and 104b are dimensioned to substantially fit within the recess 34b defined by the inner diametral edge 36a of the anvil plate 36 and the rear surface 34a of the anvil head 34. It is to be understood that the shape and size of the wound treatment material delivery pouches 104a, 104b may be varied from the exemplary configuration depicted in FIG. 4. Although two wound treatment material delivery pouches 104a, 104b are shown in a stacked configuration in FIG. 4, it is to be understood that any suitable number of pouches may be used in various configurations. For example, as illustrated in FIG. 5, in an embodiment, anvil assembly 26 includes two substantially C-shaped wound treatment material delivery pouches 302, 304 and an annular shaped wound treatment material delivery pouch 104 arranged in a stacked configuration.

Figure 7:
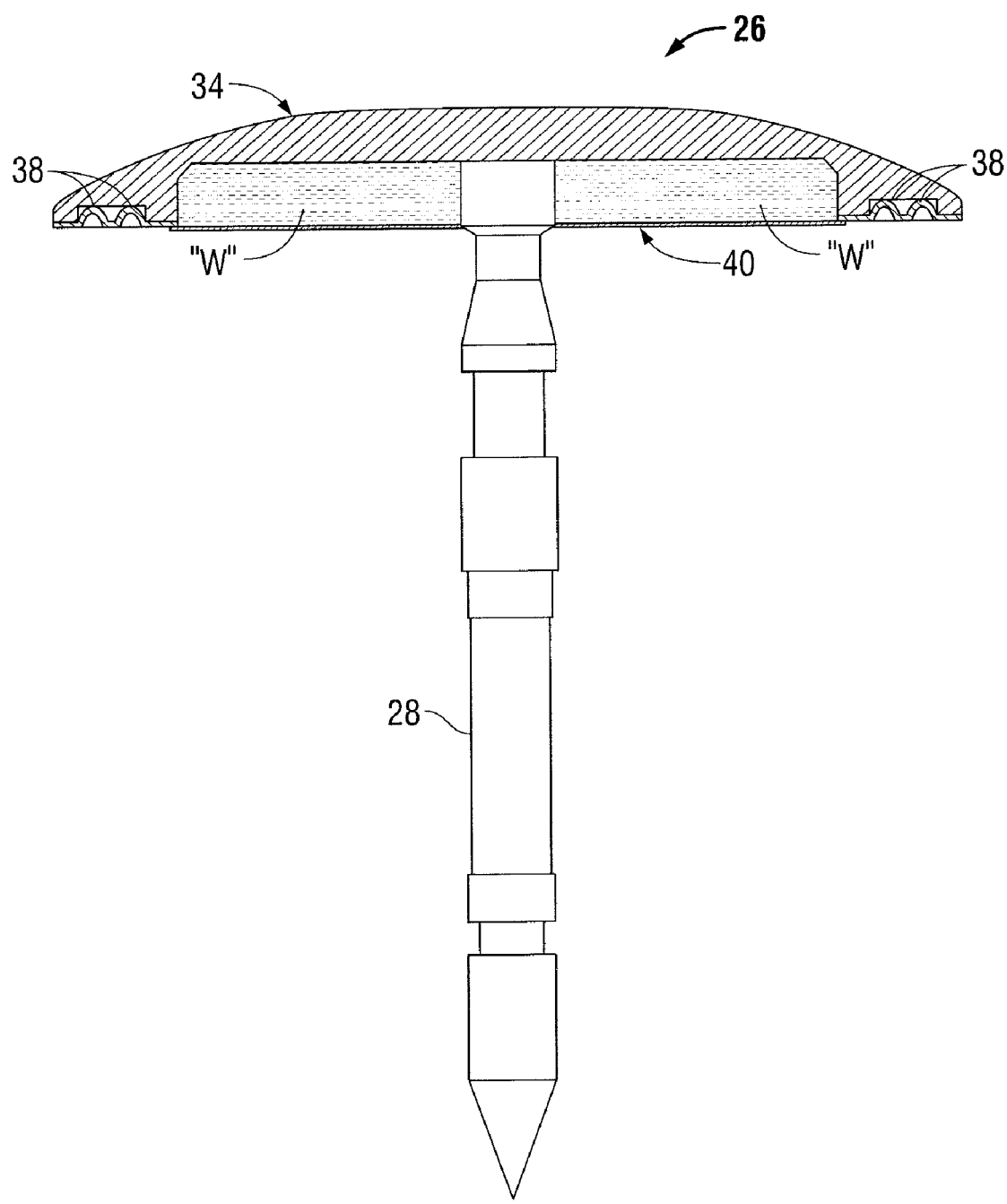
FIG. 7 is a cross-sectional view of another embodiment of the anvil assembly of FIG. 1, according to the present disclosure.

In another embodiment of the present disclosure illustrated in FIG. 7, anvil assembly 26 includes a quantity of wound treatment material "W", which is disposed in the recess 34b that is defined by the inner diametral edge 36a of the anvil plate 36 and the rear surface 34a of the anvil head 34, and a film or liner 40 so disposed as to retain/contain the wound treatment material "W" in the recess. Liner 40 is placed over or onto a portion of the surface of the anvil plate 36 and covers the entirety of the recess 34b thereby retaining the wound treatment material "W" therein. It is contemplated herein that at least a portion of the wound treatment material "W" disposed In the recess 34b of the anvil head 34 shown in FIG. 7 may contained in a wound treatment material delivery pouch.

Figure 8:
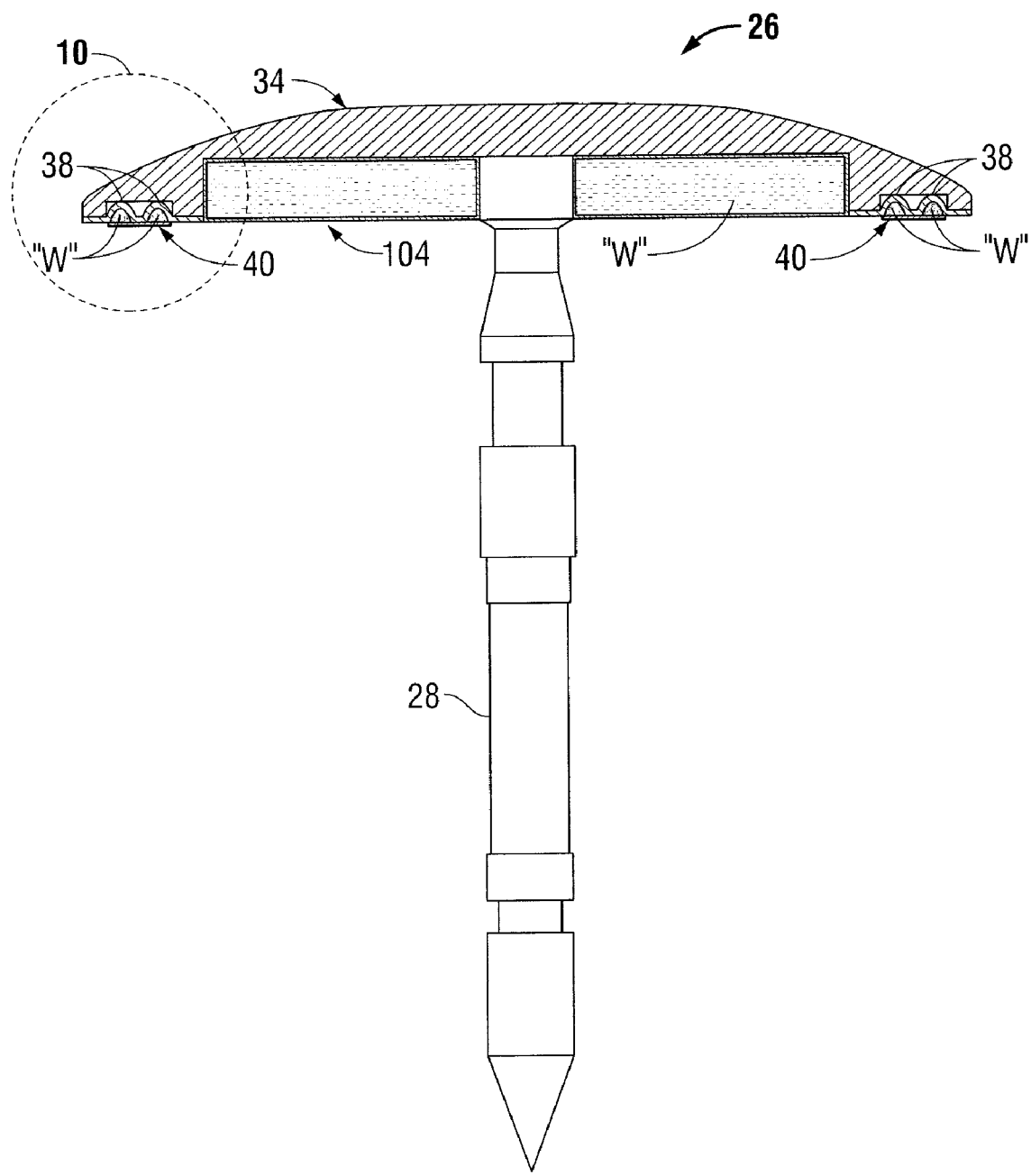
FIG. 8 is a cross-sectional view of another embodiment of the anvil assembly of FIG. 1, according to the present disclosure.

Referring now to FIGS. 8-13, in various embodiments of the presently disclosed surgical stapling device, each staple forming pocket 38 includes a quantity of wound treatment material "W" disposed therein. As seen in FIG. 8, in an embodiment, anvil assembly 26 includes a wound treatment material delivery pouch 104 (similar to FIG. 6) and each staple forming pocket 38 includes a quantity of wound treatment material "W" disposed therein. Film or liner 40 may be placed over or onto portions of the surface of the anvil plate 36, which covers the staple forming pockets 38 thereby retaining the wound treatment material "W" therein.

Figure 9:
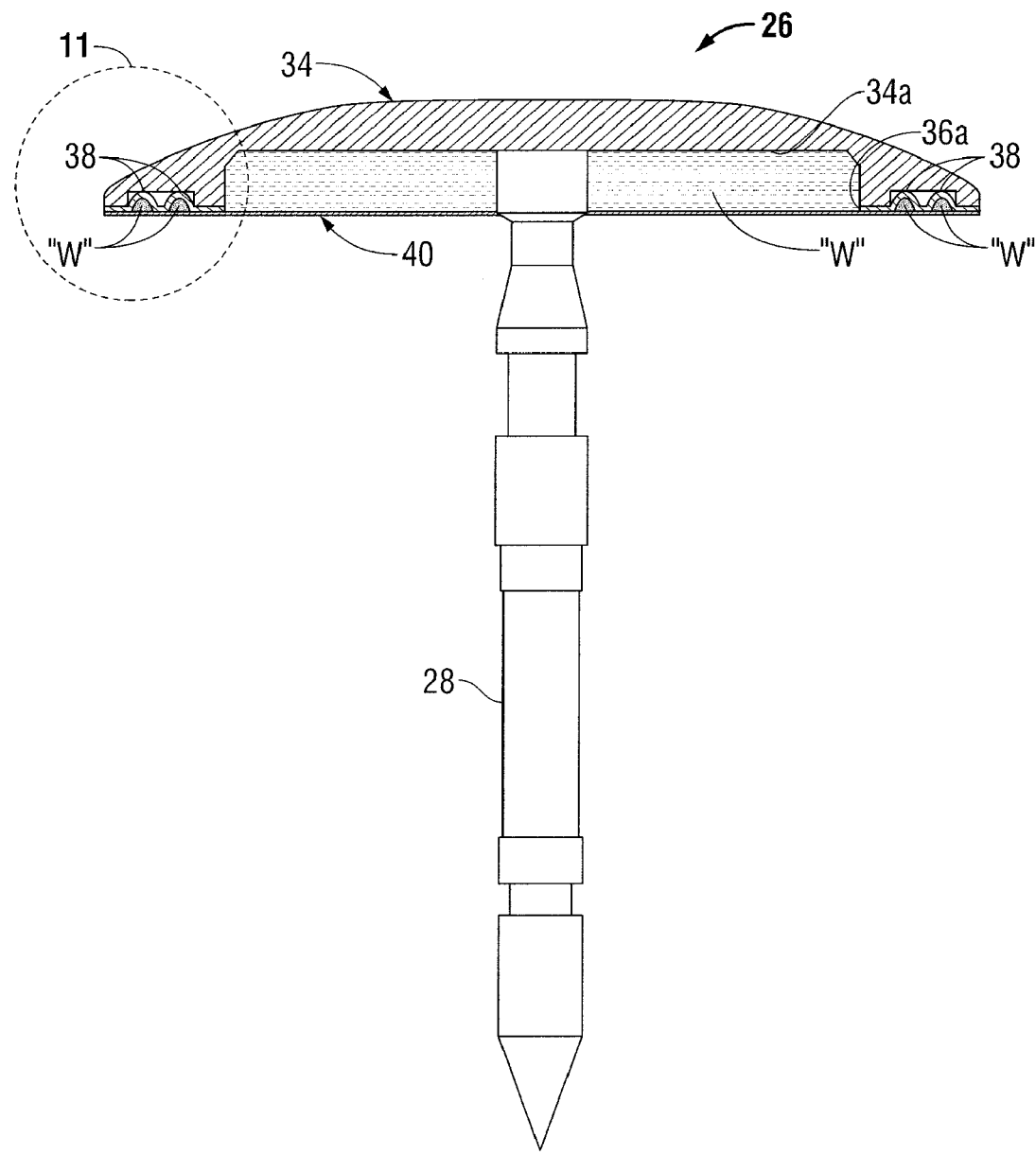
FIG. 9 is a cross-sectional view of yet another embodiment of the anvil assembly of FIG. 1, according to the present disclosure.
Figure 10:
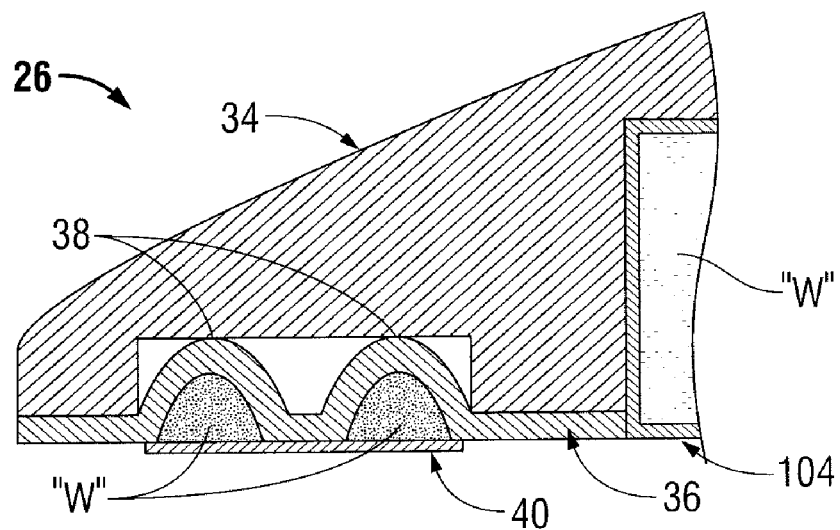
FIG. 10 is an enlarged view of the indicated area of detail of FIG. 8.
Figure 11:
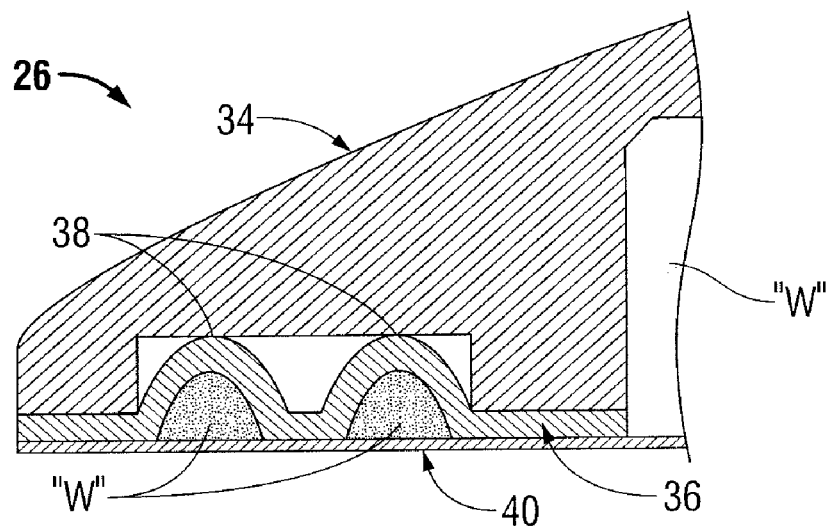
FIG. 11 is an enlarged view of the indicated area of detail of FIG. 9, according to the present disclosure.

In an embodiment of the present disclosure shown in FIGS. 9 and 11, anvil assembly 26 includes a quantity of wound treatment material "W", disposed in the recess 34b defined by the inner diametral edge 36a of the anvil plate 36 and the rear surface 34a of the anvil head 34 (similar to FIG. 7), and a film or liner 40 placed over or onto the surface of the anvil plate 36, which covers the staple forming pockets 38 thereby retaining the wound treatment material "W" therein. Although the liner 40 is shown disposed on the entire surface of the anvil plate 36 and across the recess 34b in FIG. 9, it is to be understood that the liner 40 may be configured in a variety of sizes and may be disposed on any portion of the surface of the anvil plate 36 and may cover all or any number of the staple forming pockets 38.

Figure 12:
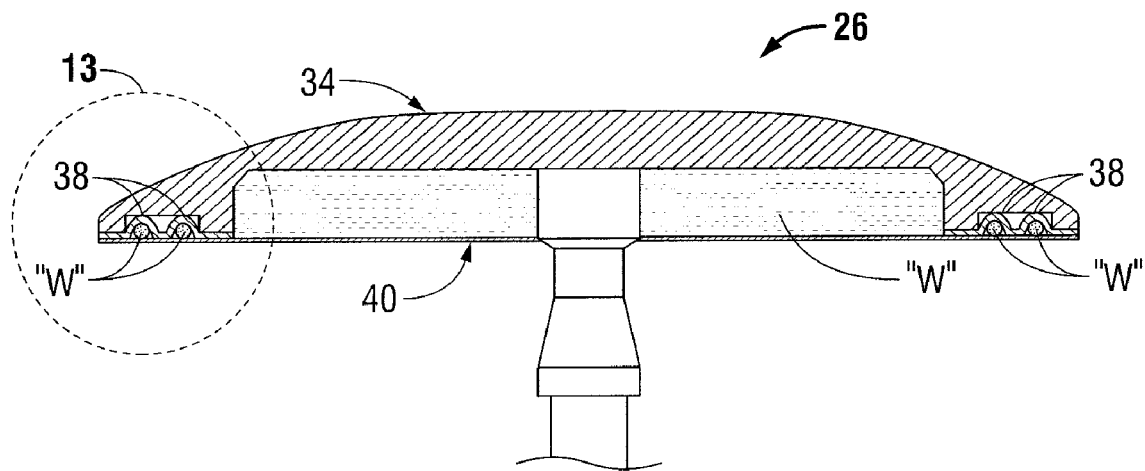
FIG. 12 is a cross-sectional view of an alternate anvil assembly, according to the present disclosure.
Figure 13:
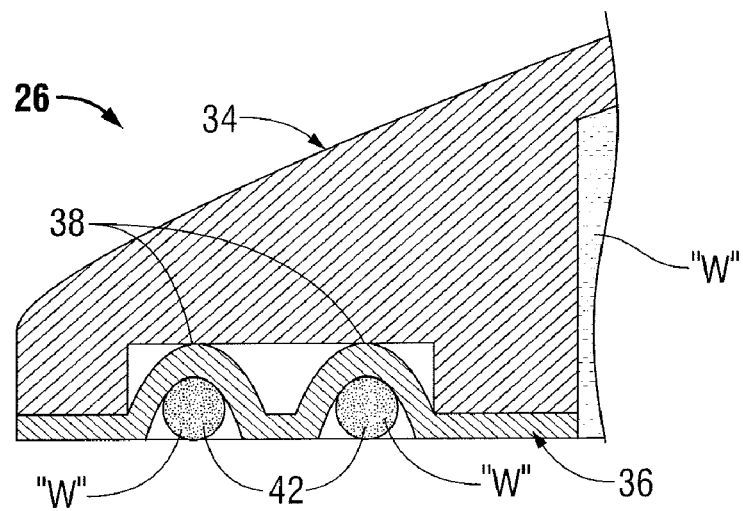
FIG. 13 is an enlarged view of the indicated area of detail of FIG. 12.

In another embodiment of the present disclosure illustrated in FIGS. 12 and 13, assembly 26 includes a quantity of wound treatment material "W", disposed in the recess 34b defined by the inner diametral edge 36a of the anvil plate 36 and the rear surface 34a of the anvil head 34 (similar to FIGS. 7 and 9) and wound treatment material "W" is contained in a capsule or liquid-gel 42 placed in each staple forming pocket 38. Each capsule 42 may be adhered to or otherwise fixedly contained in the staple forming pockets 38.

Liner 40 is fabricated from a material that can be penetrated or ruptured by surgical staples "S". For example, the finer 40 may be fabricated from a polymeric material, such as polyethylene, polyester, polyurethane or combination thereof, or other suitable material. It is contemplated herein that the liner 40 is fabricated from a bio-absorbable material so that any portion of the liner 40 that remains in the patient's body following the surgical procedure will be absorbed into the body.

FIGS. 14 and 15A-15C illustrate the use of the surgical stapling device 10 and detachable anvil assembly 26 in an anastomosis procedure to effect joining of the adjacent intestinal sections "$T_1$" and "$T_2$". The anastomosis procedure is typically performed using minimally invasive surgical techniques including, for example, laparoscopic procedures and instrumentation. At the point in the procedure shown in FIG. 14, a diseased intestinal section has been previously removed, the anvil assembly 26 has been applied to the operative site, either through a surgical incision or transanally, and positioned within the first intestinal section "$T_1$", and the tubular body portion 14 of the surgical stapling device 10 has been inserted transanally into second intestinal section "$T_2$". Intestinal sections "$T_1$" and "$T_2$" are also shown temporarily secured about their respective components, i.e., shaft 28 of the anvil assembly 26, and the distal end of tubular body portion 14, by a suitable method such as a purse string suture (not shown).

The surgeon then maneuvers the anvil assembly 26 until a proximal end of the shaft 28 is operatively connected to the rod member 21 of the tubular body portion 14. Thereafter, the anvil assembly 26 and the tubular body portion 14 are approximated to approximate intestinal sections "$T_1$" and "$T_2$".

Figure 15A:
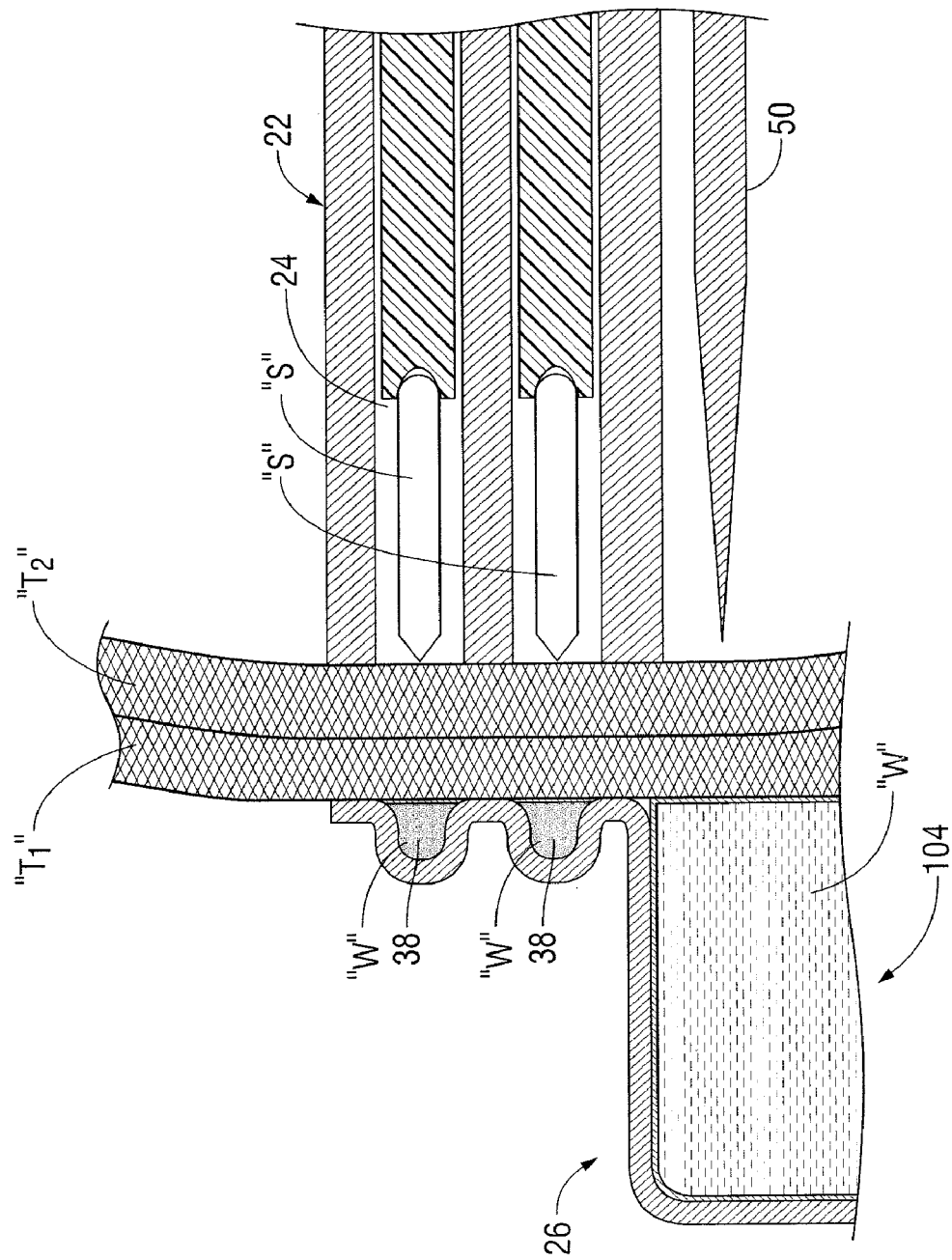
FIG. 15A is an enlarged detail view of the surgical stapling device of FIG. 1 positioned in the target surgical site immediately prior to the firing of the surgical stapling device.

With reference to FIGS. 14 and 15A, with the anvil assembly 26 approximated toward the staple cartridge assembly 22 and the intestinal sections "$T_1$" and "$T_2$" clamped or captured therebetween, the staple forming pockets 38 of the anvil assembly 26 are in registration with the staple retaining slots 24 of staple cartridge assembly 22. In particular, the staples "S", retained in the staple retaining slots 24, are in registration with the staple forming pockets 38 of anvil assembly 26.

Figure 15B:
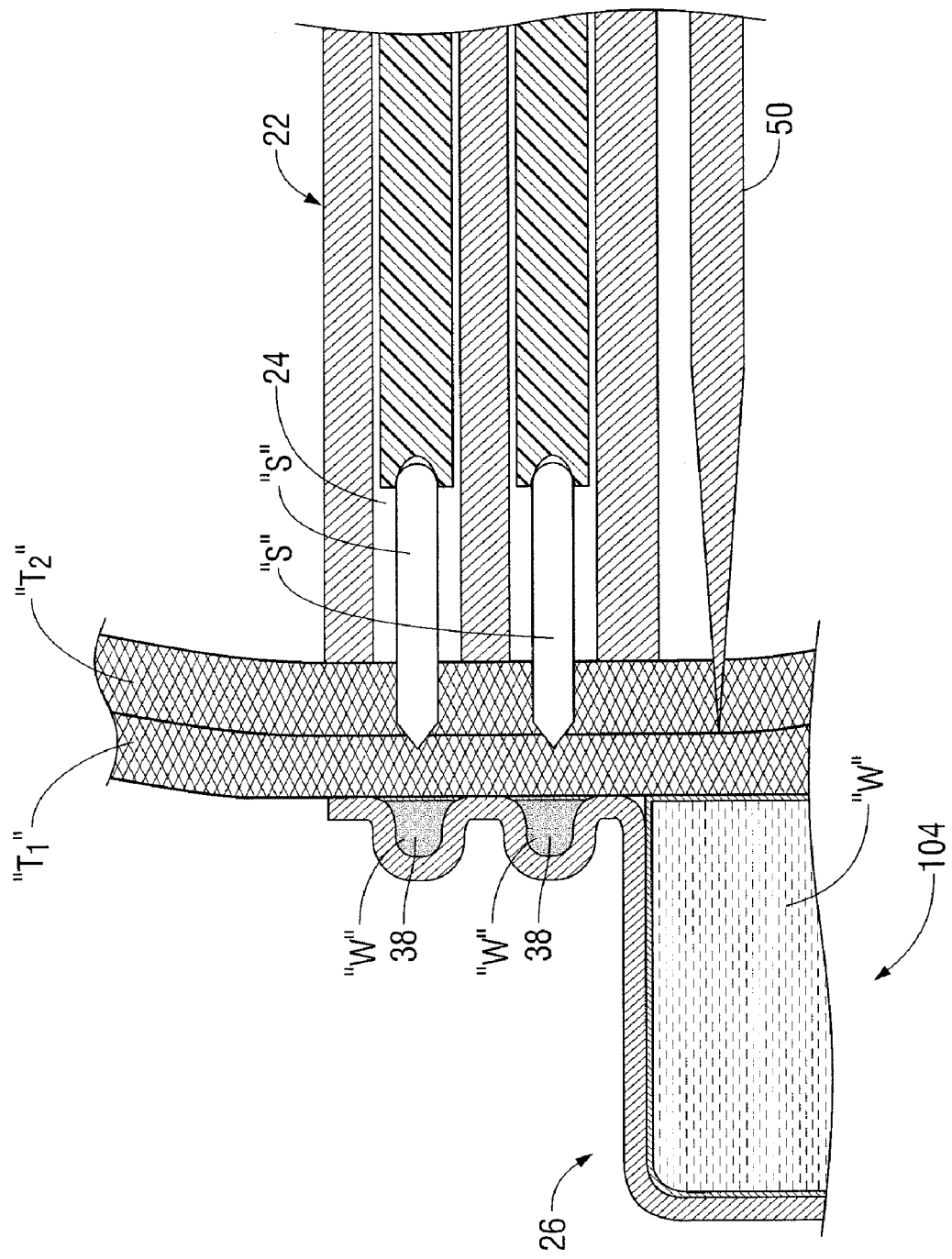
FIG. 15B is an enlarged detail view of the surgical stapling device of FIG. 1 positioned in the target surgical site upon an initial stage of the firing of the surgical stapling device.
Figure 15C:
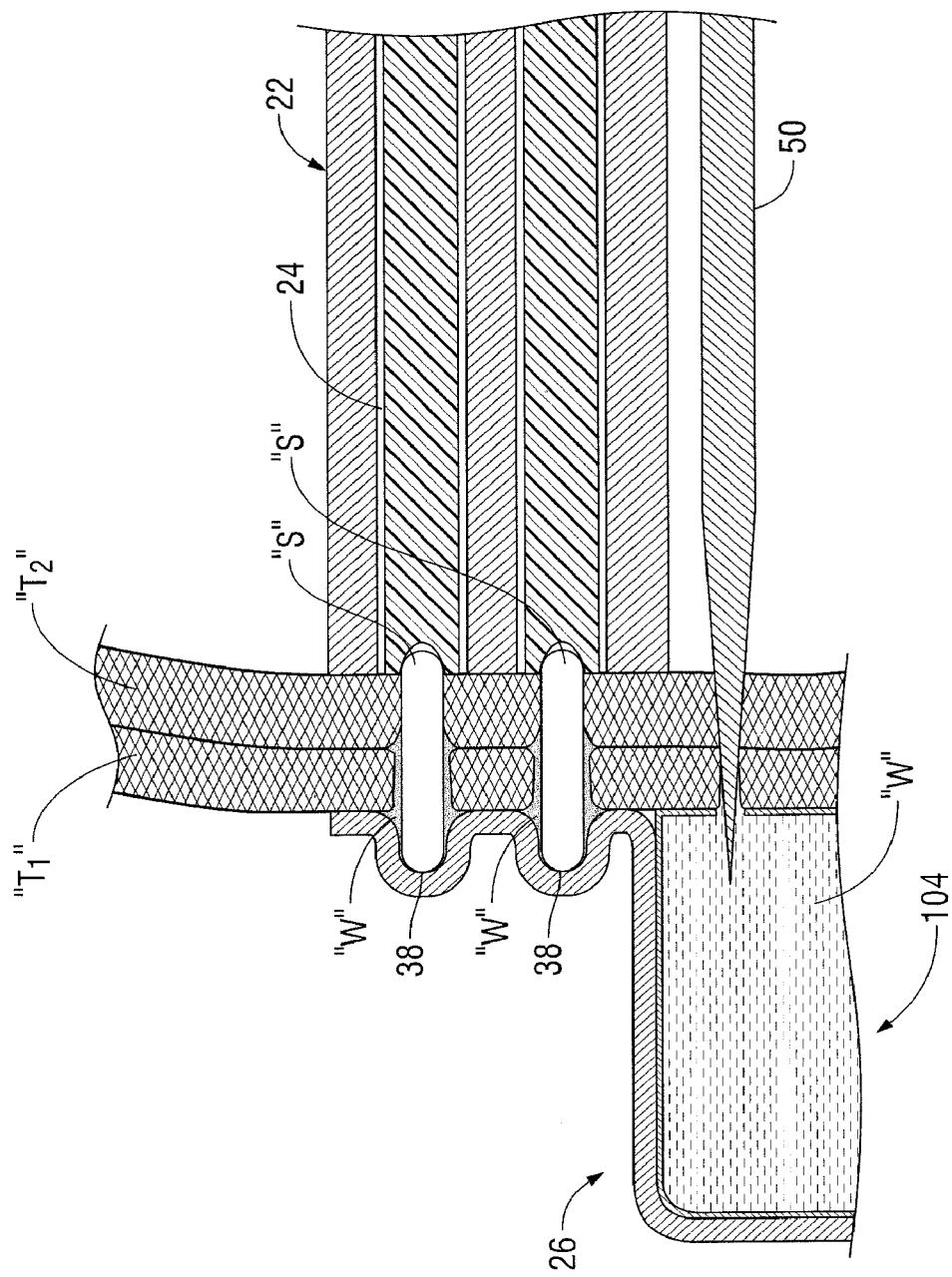
FIG. 15C is an enlarged detail view of the dispensing of wound treatment material from the anvil assembly upon a further stage of the firing of the surgical stapling device.

With anvil assembly 26 so positioned relative to the staple cartridge assembly 22, the surgical stapling device 10 is fired, thereby stapling and adhering intestinal sections "$T_1$" and "$T_2$" to one another. As illustrated in FIGS. 15B and 15C, upon firing of the surgical stapling device 10, the staples "S" are driven from the staple cartridge assembly 22 and driven through the intestinal sections "$T_1$" and "$T_2$" thereby mechanically securing the intestinal sections "$T_1$" and "$T_2$" to one another. As the staples "S" are driven through the intestinal sections "$T_1$" and "$T_2$", the staples "S" penetrate the liner 40 and release the wound treatment material "W" contained in staple forming pockets 38 of the anvil plate 36 onto the intestinal tissue "$T_2$". The wound treatment material "W" spreads along staples "S" to the interface between the intestinal tissues "$T_1$" and "$T_2$". In this manner, where the wound treatment material "W" contains an adhesive, the wound treatment material "W" helps to adhere the intestinal sections "$T_1$" and "$T_2$" to one another.

It is contemplated herein that that the wound treatment material "W" may function to reduce the seepage of blood at or on the anvil side of the staple "S" (e.g., in first intestinal tissue "$T_1$"), as compared to surgical apparatus having an anvil assembly with no wound treatment material. In an embodiment of the presently disclosed surgical stapling device 10, as the staples "S" are driven into the staple forming pockets 38 of the anvil assembly 26, the wound treatment material "W" is displaced into the area surrounding staples "S". Substantially simultaneously therewith, the knife blade 50 severs the portions of the intestinal sections "$T_1$" and "$T_2$" located radially inward of the knife blade 50.

Figure 16:
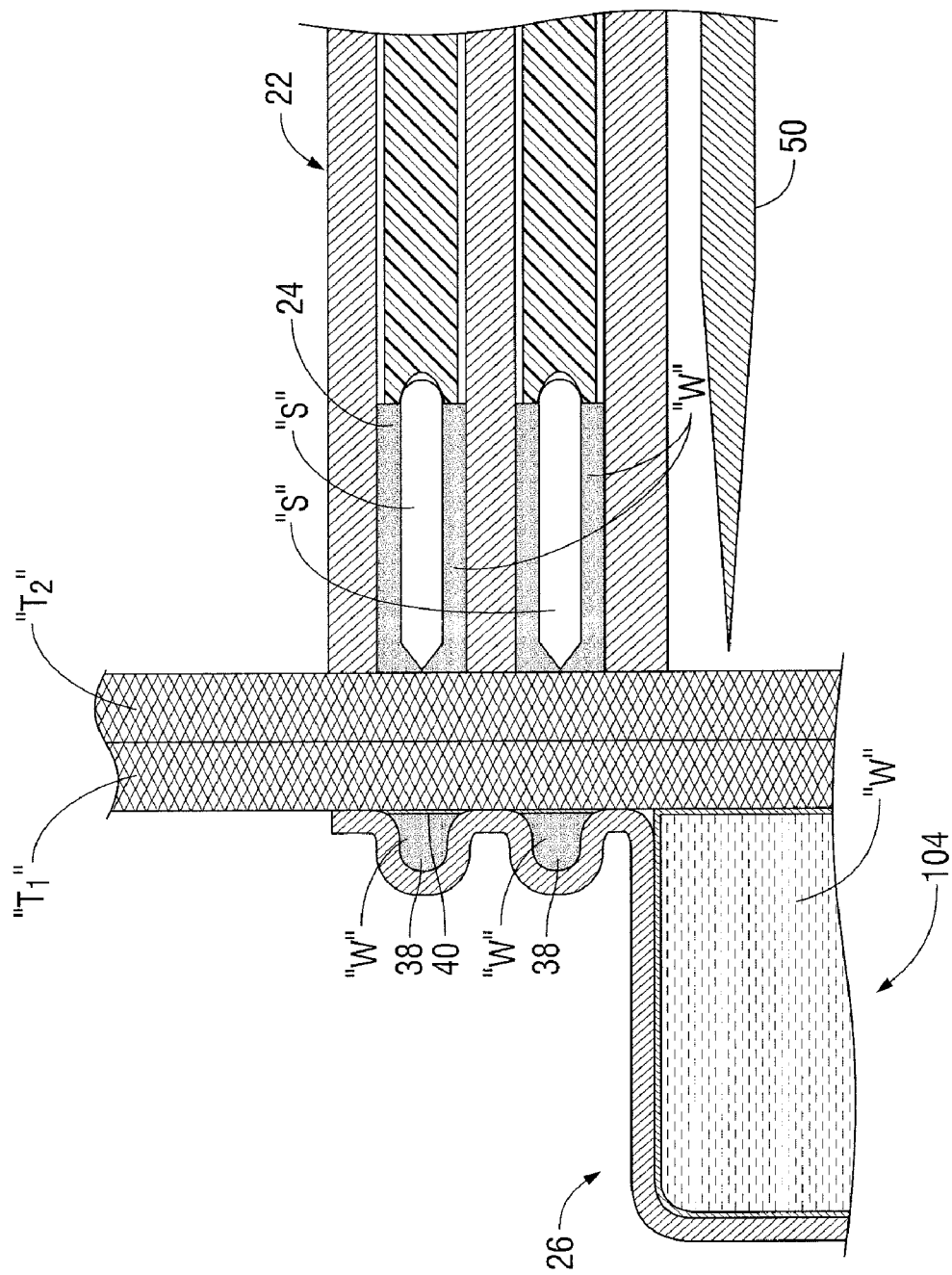
FIG. 16 is an enlarged detail view of the anvil assembly of FIGS. 2A, 2B and 8 and a staple cartridge assembly of a surgical stapling device according to another embodiment of the present disclosure, positioned in the target surgical site, prior to the firing of the surgical stapling device.

Turning now to FIG. 16, in an alternate embodiment, the wound treatment material "W", including a sealant, may be disposed within (e.g., loaded into, packed into, etc.) the staple retaining slots 24. In operation, when the surgical stapling device 10 is fired, the wound treatment material "W" is dispensed onto or otherwise spread onto the area of the second intestinal section "$T_2$" surrounding a backspan of staples "S".

Figure 17:
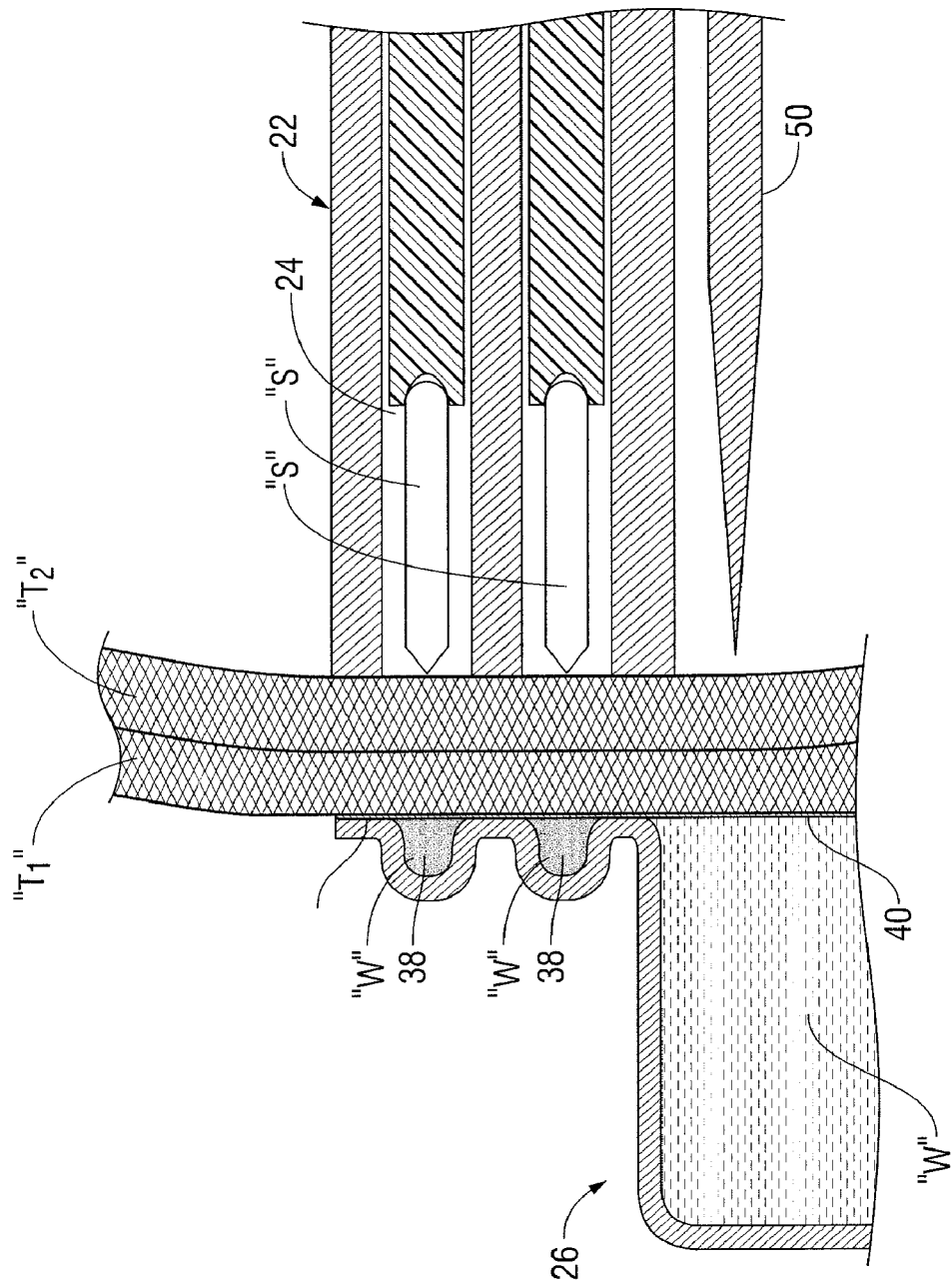
FIG. 17 is an enlarged detail view of the anvil assembly of FIG. 9 and a staple cartridge assembly of a surgical stapling device according to an embodiment of the present disclosure, positioned in the target surgical site, prior to the firing of the surgical stapling device.

FIG. 17 is an enlarged detail view of the anvil assembly of FIG. 9 and a staple cartridge assembly of a surgical stapling device according to an embodiment of the present disclosure, positioned in the target surgical site, prior to the firing of the surgical stapling device. In operation, when the surgical stapling device 10 is fired, the staples "S" are driven into the staple forming pockets 38, rupturing the liner 40 covering the staple forming pockets 38 and the wound treatment material "W" is dispensed onto or otherwise spread onto the area of the second intestinal section "$T_2$" surrounding a backspan of staples "S". Substantially simultaneously therewith, the knife blade 50 severs the portions of the intestinal sections "$T_1$" and "$T_2$" located radially inward of the knife blade 50 and ruptures the liner 40 and the wound treatment material "W" contained within the recess 34b of anvil head 34 is dispensed.

Figure 18:
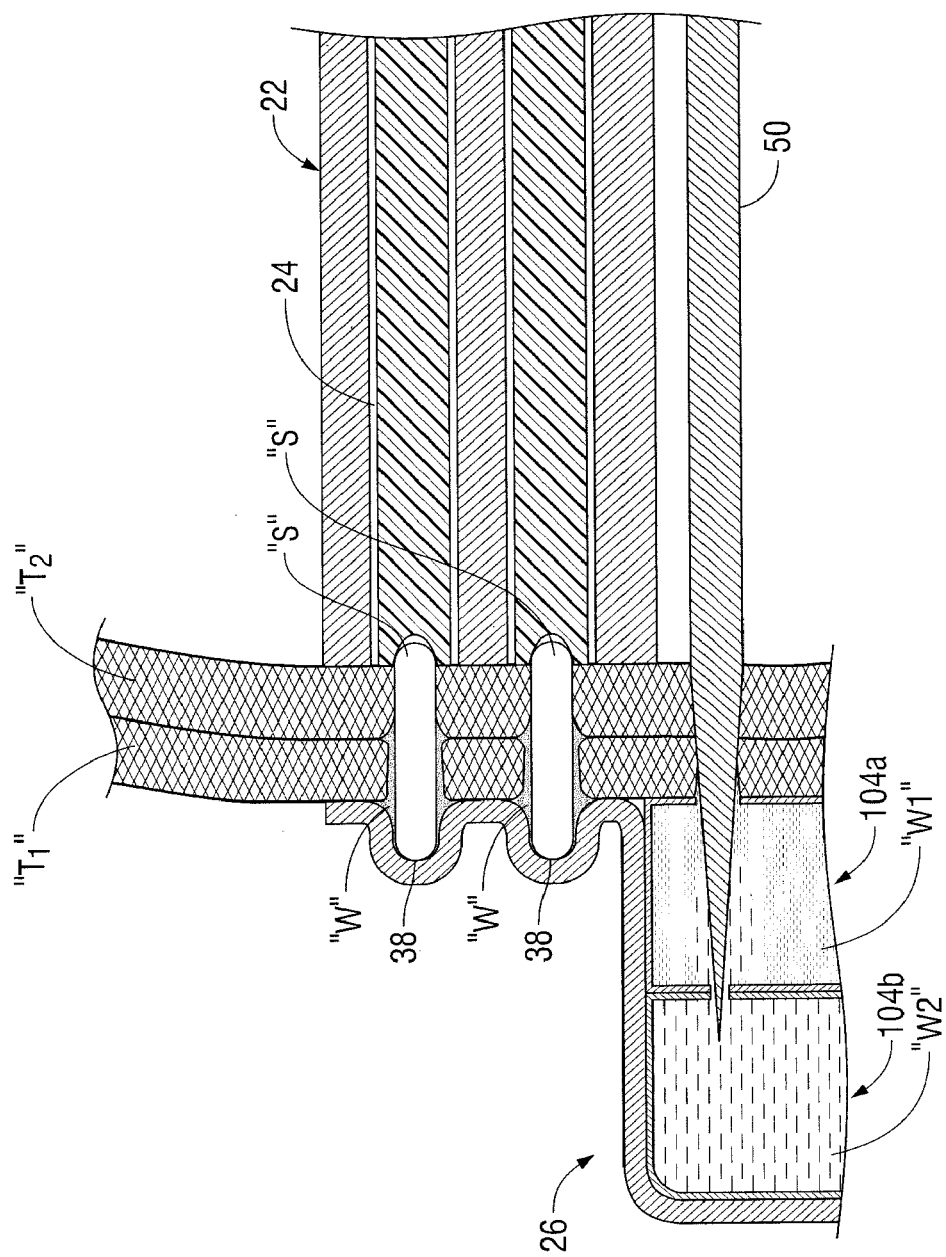
FIG. 18 is an enlarged detail view of the anvil assembly of FIGS. 3A and 3B and a staple cartridge assembly of a surgical stapling device according to an embodiment of the present disclosure, positioned in the target surgical site, following the firing of the surgical stapling device.

FIG. 18 is an enlarged detail view of the anvil assembly of FIG. 4 and a staple cartridge assembly of a surgical stapling device according to an embodiment of the present disclosure, positioned in the target surgical site, upon the firing of the surgical stapling device. In operation, when the surgical stapling device 10 is fired, the knife blade 50 severs the portions of the intestinal sections "$T_1$" and "$T_2$" located radially inward of the knife blade 50 and ruptures the wound treatment material delivery pouches 104a and 104b, whereby a first wound treatment material "W1", e.g., adhesive, contained within the wound treatment material delivery pouch 104b mixes with a second wound treatment material "W2", e.g., resin, contained within the wound treatment material delivery pouch 104a, and the activated mixture of the first and second wound treatment materials is dispensed.

Although exemplary embodiments of the present disclosure have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing exemplary embodiments may be made without departing from the scope of the disclosure.

What is claimed is:

1. An anvil assembly for a circular stapling device, the anvil assembly comprising:
   an anvil head configured to support an anvil plate thereon;
   a shaft extending from the anvil head and configured to selectively engage a rod member of the circular stapling device;
   an anvil plate operatively connected to the anvil head, wherein the anvil plate includes an inner diametral edge, and wherein the anvil plate defines a plurality of staple forming pockets therein at a location radially outward of the inner diametral edge;
   a recess formed in the anvil head, wherein the recess is defined by the inner diametral edge of the anvil plate and a rear surface of the anvil head; and a wound treatment material disposed substantially within the recess.

2. The anvil assembly of claim 1, wherein the wound treatment material is contained in at least one wound treatment material delivery pouch.

3. The anvil assembly of claim 2, wherein the recess has a diameter larger than a diameter of a knife blade that is longitudinally moveable along the shaft, wherein the wound treatment material delivery pouch is at least partially axially aligned with the knife blade.

4. The anvil assembly of claim 1, wherein the wound treatment material is at least one of an adhesive, a sealant, a hemostat and a medicament.

5. The anvil assembly of claim 4, wherein the adhesive includes at least one of an adhesive which cures upon tissue contact, an adhesive which cures upon exposure to ultraviolet (UV) light, and an adhesive which is pressure sensitive.

6. The anvil assembly of claim 4, wherein the adhesive includes at least one of a protein derived, aldehyde-based adhesive material, and a cyanoacrylate-based material.

7. The anvil assembly of claim 4, wherein the sealant material includes at least one of a fibrin sealant material, a collagen-based and synthetic polymer-based tissue sealant material, and synthetic polyethylene glycol-based, hydrogel sealant material.

8. The anvil assembly of claim 4, wherein the hemostat material includes at least one of a fibrin-based material, a collagen-based material, an oxidized regenerated cellulose-based material, a gelatin-based material, and a fibrinogen-thrombin material.

9. The anvil assembly of claim 4, wherein the medicament includes at least one of drugs, enzymes, growth factors, peptides, proteins, dyes, and diagnostic agents.

10. The anvil assembly of claim 1, further comprising a wound treatment material disposed in each staple forming pocket of the anvil plate.

11. The anvil assembly of claim 10, further comprising a liner covering the plurality of staple forming pockets.

12. The anvil assembly of claim 1, wherein the wound treatment material is disposed within an annular pouch.

13. A surgical stapling device, comprising:
a handle portion;
a body portion located at the distal end of the handle portion;
a head portion located at the distal end of the body portion, the head portion including an anvil assembly, a staple cartridge assembly and a knife blade, wherein the staple cartridge assembly includes an annular array of staples, wherein the anvil assembly includes:
an anvil head configured to support an anvil plate thereon;
a shaft extending from the anvil head and configured to selectively engage a rod member of the staple cartridge assembly;
an anvil plate operatively connected to the anvil head, wherein the anvil plate includes an inner diametral edge having a diameter larger than a diameter of the knife blade, and wherein the anvil plate defines a plurality of staple forming pockets therein;
a recess formed in the anvil head, wherein the recess is defined by the inner diametral edge of the anvil plate and a rear surface of the anvil head; and
a wound treatment material disposed substantially within the recess.

14. The surgical stapling device of claim 13, wherein the wound treatment material is contained in at least one wound treatment material delivery pouch.

15. The surgical stapling device of claim 13, wherein the wound treatment material is contained in a pair of stacked wound treatment material delivery pouches.

16. The surgical stapling device of claim 15, wherein the pair of stacked wound treatment material delivery pouches are at least partially axially aligned with the knife blade.

17. The surgical stapling device of claim 16, wherein at least one of the pair of stacked wound treatment material delivery pouches includes a plurality of compartments.

18. The surgical stapling device of claim 13, wherein the wound treatment material is contained in a plurality of wound treatment material delivery pouches, and wherein at least one wound treatment material delivery pouch includes a plurality of compartments.

19. The surgical stapling device of claim 13, further comprising a liner covering the entirety of the recess and disposed over the wound treatment material.

20. The surgical stapling device of claim 19, wherein at least a portion of the wound treatment material is contained in a wound treatment material delivery pouch.

* * * * *